United States Patent [19]

El Alaoui et al.

[11] Patent Number: 6,124,109
[45] Date of Patent: Sep. 26, 2000

[54] SYSTEM FOR QUALITATIVELY AND/OR QUANTITATIVELY ANALYZING PREFERABLY BIOLOGICAL SUBSTANCES USING ENHANCED CHEMILUMINESCENCE, AND METHOD AND ANALYSIS KIT USING SAME

[75] Inventors: Said El Alaoui, Saint-Bonnet-de-Mure; Loic Blum, Caluire; Robert Henry, Lyons, all of France

[73] Assignee: Innogenetics N.V., Belgium

[21] Appl. No.: 09/051,761

[22] PCT Filed: Oct. 18, 1996

[86] PCT No.: PCT/FR96/01636

§ 371 Date: May 9, 1998

§ 102(e) Date: May 9, 1998

[87] PCT Pub. No.: WO97/15684

PCT Pub. Date: May 1, 1997

[30] Foreign Application Priority Data

Oct. 20, 1995 [FR] France ................................. 95/12607

[51] Int. Cl.$^7$ ............... G01N 33/535; G01N 33/532; G01N 33/545
[52] U.S. Cl. ............... 435/7.92; 435/7.71; 435/7.72; 435/7.9; 435/960; 435/962
[58] Field of Search ....................... 435/7.9, 7.92, 435/7.71, 7.72, 960, 962

[56] References Cited

U.S. PATENT DOCUMENTS

| 4,598,044 | 7/1986 | Kricka et al. | 435/28 |
|---|---|---|---|
| 5,043,266 | 8/1991 | Dewar et al. | 435/7.9 |
| 5,206,149 | 4/1993 | Oyama et al. | 435/28 |

FOREIGN PATENT DOCUMENTS

| 296752 | 12/1988 | European Pat. Off. . |
|---|---|---|
| 505198 | 9/1992 | European Pat. Off. . |

OTHER PUBLICATIONS

Blum et al, NATO ASI Ser., Ser. 2 38 (Biosensors for Direct Monitoring of Environmental Pollutants in Field), 271–280 (1997).

Analytical Letter, vol. 27, No. 6, Jan. 1, 1994 pp. 1189–1122, XP 000568630, Hori et al, "A New . . . Luminometer".

*Primary Examiner*—Mary E. Ceperley
*Attorney, Agent, or Firm*—Bierman, Muserlian and Lucas

[57] ABSTRACT

The field of the present invention is that of identification and analysis of chemical and/or biological species of the enzyme/substrate, enzyme/inhibitor or antigen/antibody etc. type. The problem on which the invention is based is to provide a system for qualitative and/or quantitative analysis of biological substances by amplified chemiluminescence which allows an actual significant improvement in the emission of light resulting from passage of a chemiluminescent reagent to the excited state. This problem has been solved by means of a system according to the invention, which involves a ligand a) which can be coupled with the substances to be analysed, a chemiluminescent reagent b) of the luminol type, an enzyme c), a substrate d) which oxidizes the enzyme c), and at least one amplifier e), this system being characterized in that the amplifier e) is chosen from the family of halogenophenol (iodophenol) esters. The invention also relates to an analytical method using this system and to an analytical kit comprising the said system.

15 Claims, 2 Drawing Sheets

SYSTEM FOR QUALITATIVELY AND/OR QUANTITATIVELY ANALYZING PREFERABLY BIOLOGICAL SUBSTANCES USING ENHANCED CHEMILUMINESCENCE, AND METHOD AND ANALYSIS KIT USING SAME

TECHNICAL FIELD

The field of the present invention is that of analytical chemistry, a field of interest, more particularly, for identification and analysis of chemical species, preferably biological species, and in particular high molecular weight species, such as nucleic acids, or also biopolymers of a protein nature, e.g.: enzymes/substrates and antigens/antibodies.

More precisely, the present invention relates to:

firstly, a system for qualitative and/or quantitative analysis of substances, preferably biological substances, by amplified chemiluminescence, secondly, an analytical method using this system, and thirdly, an analytical kit comprising the said system.

Substances or biological species, more particularly but not limitatively, envisaged by the invention are the nucleic acids RNA and DNA and any genetic structure containing them, as well as compounds which are capable of being involved in immunological antigen (Ag)/antibody (Ab) reactions, and furthermore products which couple to one another in the context of a mechanism of recognition and enzymatic reaction: enzyme/substrate, enzyme/inhibitor, receptor/ligand and lectin/sugar.

PRIOR ART

To detect, identify or analyse this type of molecule or structure, it is conventional to use their property of bioaffinity, that is to say their peculiar capacity for coupling specifically with their complements by mechanisms of genetic hybridization or immunological or enzymatic recognition.

Chemiluminescence, and more specifically also that which is so-called amplified, is one of the analytical techniques which proceeds by this principle and which is currently used in the laboratory.

Detection by amplified chemiluminescence can be found in the context of well-known analytical procedures of the "western blot" type or of the "ELISA" type as regards proteins, or also "southern & northern blot" type as regards RNA and DNA.

This technique of amplified chemiluminescence is an advantageous and promising alternative compared with conventional immunological analyses in which radioactive isotopes are used as the marker and indicator of the coupling under consideration. In fact, radioanalysis is starting to become out-of-date, since it has a large number of disadvantages, including, in particular:

hazardous manipulation, low useful storage life of the radioactively labelled substance, difficulty of radioactive labelling, and treatment of radioactive waste.

Unfortunately, the development of these analytical techniques by amplified chemiluminescence has been slowed down because of the limited sensitivity of the systems which currently exist. This sensitivity depends in part on the light emitted in the course of and at the end of the luminescence reaction which indicates the couplings under consideration.

At this stage of the description, it appears useful to state the concepts by recording the principles of detection by amplified chemiluminescence. Firstly, luminescence can be defined as being the emission of light resulting from the restoration of part of the energy emanating from a substance in an excited state. In chemiluminescence, the excitation results from a chemical reaction. The latter is triggered following coupling of a ligand, directly or indirectly, with one or more substances, preferably biological substances, to be analysed. This ligand is one of the elements of an analytical system comprising, in addition, a chemiluminescent reagent, an enzyme or catalytic subunits of chemiluminescence, and a substrate which is specific to this enzyme or the catalytic subunit or subunits and is capable of being converted under the effect thereof into at least one initiator of the excitation of the luminescent reagent, this excitation being accompanied by the production of light.

One of the systems used the most in amplified chemiluminescence is that at the heart of which is found chemical reactions of reagents of the cyclic diacylhydrazide type, such as luminol or isoluminol. In such a system, the enzymes used are, for example, peroxidases, which are capable of converting a substance called an oxidant, such as $H_2O_2$, into an initiator of the oxidation of luminol. Since this oxidation produces too few photons, the excitation of luminol cannot be detected with a significant sensitivity, and it is therefore necessary to amplify this oxidation reaction.

Among the most effective amplifiers known, there may be mentioned those which belong to the family of halogenophenols and their derivatives. However, as already indicated above, the performances achieved with the aid of such amplifiers remain notably insufficient, in particular with regard to the amount of light emitted after the reaction.

There are several previous technical proposals which deal in vain with this problem.

Thus, the patent EP 0 116 454 discloses a system for chemiluminescence analysis in which the luminescent reaction takes place between a peroxidase, an oxidant and a chemiluminescent reagent in the form of luminol: 2,3-dihydro-1,4-phthalazinedione. The invention protected in this patent proposes the use of an amplifier consisting of, in particular, 4-iodophenol, 4-bromophenol, 4-chlorophenol and other phenol derivatives, such as 4-hydroxycinnamic acid, 2-naphthol, 6-bromonaphth-2-ol and 4-hydroxyphenyl disulphide, among others. These amplifiers allow an improvement in the emission of the light and, more particularly, the signal/background noise ratio. However, the better signal/noise ratio with the aid of these amplifiers remains insufficient with regard to the sensitivity of the method. This causes an increase in the volume of amplifiers used to obtain a sufficient sensitivity. This results in possible disturbances in the reaction and an undeniable increase in the cost of the analysis.

To attempt to perfect this known system, new chemiluminescence amplifiers were subsequently proposed through the international patent application PCT WO 91/05 872. The latter are intended to be used in a system comprising luminol as the reagent, a peroxidase as the enzyme and $H_2O_2$ as the oxidizing substrate. The said means of amplification consist of inactive precursors chosen from the family of esters of p-halogenophenols, e.g. iodophenols. The activation of these precursors of amplifiers is realized with the aid of an esterase when all the components of the chemiluminescence system are brought together, in order to obtain the production of light, which will serve as a detection indicator. According to the inventors mentioned in this PCT application, the coupling realized in this way between a chemiluminescence enzyme and an enzyme which activate the amplifier is the cause of an amplification phenomenon of a nature which improves the sensitivity of the analysis. However, even here, the improvements obtained remain insufficient.

The patent application EP 0 516 948 also discloses chemiluminescence amplifiers for the system luminol/$H_2O_2$/peroxidase which consist of esters of the formula ArOX, in which X is a masking group which can be activated under the action of a hydrolytic enzyme and Ar is an aromatic group. These are also inactive precursors of amplifiers, which are capable of being converted into active products under the effect of an enzyme, which can be, for example, an esterase in the case where these pre-amplifiers are esters. Disodium phosphate esters of iodophenol, acetic esters of diphenol and, finally, exolydic derivatives of iodophenol and diphenol are mentioned in particular in this application. The amplification means described in this European patent application do not produce better results than those according to the application PCT WO 91/05 872 mentioned above.

The previous reference "Analytical Letters, 27(6), 1109–1122, (1994)" by H. HORI et al. also describes new phenolic amplifiers of chemiluminescence in the context of their luminol/$H_2O_2$/peroxidase reaction. These new amplifiers are 4-hydroxybenzylidene-cyclopentenediones on the one hand and 4-hydroxybenzylidene-malononitriles on the other hand.

The improvements in the emission of light which are obtained with these amplifiers remain inferior to those found for p-iodophenol described before. Furthermore, the related study in this article reveals a change in trend in the context of development of new amplifiers. In fact, the works on inactive esters derived from halogenophenols are no longer in vogue.

Finally, the international patent application PCT WO 94/23 060 proposes a method for amplification of the chemiluminescence reaction involving luminol, a peroxidase, an oxidizing substrate (=$H_2O_2$) and an amplifier intended for increasing the signal/noise ratio of luminous emissions. The amplifier consists of a combination of an organoboron compound and a non-boron organic compound. The organoboron compound corresponds to the formula ArB(OR)$_2$, in which Ar=a substituted or unsubstituted aromatic group. The non-boron organic compound of the amplification is a halogenophenol derivative of the type of those mentioned above in the other references of the prior art. Once again, the improvement in the signal/noise ratio obtained with the invention described in this application WO 94/23 060 is not of significant interest.

BRIEF DESCRIPTION OF THE INVENTION

In this state of knowledge, one of the essential objects of the present invention is to provide a system for qualitative and/or quantitative analysis of substances, preferably biological substances, by amplified chemiluminescence which allows an actual and significant improvement in the emission of light resulting from passage of a chemiluminescent reagent to the excited state.

Another essential object of the invention is to provide a system for amplified chemiluminescence of the type of that above, which is simple to use and economical.

Another essential object of the invention is to provide a system for analysis by chemiluminescence of the type of those comprising luminol or analogues as the luminescent reagent, a peroxidase as the luminescence enzyme, a peracid or peroxide, such as $H_2O_2$, as the oxidizing substrate and, in addition, an amplifier belonging to the family of phenol derivatives, which system should be perfectly effective at a low dose, with respect to the level of luminescence obtained.

Another essential object of the invention is to provide a method for the qualitative and/or quantitative analysis of substances, preferably biological substances, by chemiluminescence which obtains the abovementioned light emission and sensitivity performances.

Another essential object of the invention is to provide a kit for analysis by chemiluminescence using the said system and the said method.

In the search to achieve these objects, the applicant has succeeded in demonstrating, after several research works and experiments and quite surprisingly and unexpectedly, that it is appropriate to choose the amplifier from the sub-family of esters derived from phenol, the said esters being distinguished by their characteristic of being not readily hydrolysable.

It follows from this that the present invention firstly relates to a system for qualitative and/or quantitative analysis of substances, preferably biological substances, by amplified chemiluminescence, a system of the type of those which involve, essentially:

a) at least one ligand which is capable of coupling with the substance or substances to be analysed, b) at least one chemiluminescent reagent which belongs to the family of cyclic diacylated dihydrazides fused to an aromatic radical, c) at least one enzyme, d) at least one oxidizing substrate which is specific to the enzyme (c) and is capable of being converted, under the effect thereof, into at least one initiator of the oxidation of reagent (b) with production of light, e) and at least one amplifier of the luminescence reaction, characterized:

in that the amplifier (e) corresponds to the following general formula:

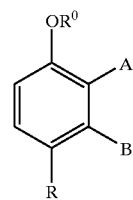

(1)

in which:

R$^0$ is a functionalized or non-functionalized linear or branched C$_1$–C$_{10}$ radical, R$^0$ being preferably selected from the following radicals:

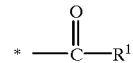

where R$^1$ corresponds:

1i■ to a linear or branched C$_1$–C$_{10}$ alkyl radical, advantageously a methyl, a propyl, a butyl, a pentyl or a hexyl;

2i■ to a C$_1$–C$_{10}$ alkylcarboxyl substituent, advantageously alkylmonocarboxyl, the substituents malonyl, succinyl, glutaryl, adipyl, heptanoyl, maleyl or fumaryl being particularly preferred alkylmonocarboxyls;

3i■ to alkylamine or aminoalkyl;

4i∎ to aryl, aralkyl or alkylaryl, preferably phenyl;

\* or a radical of a (poly)organosiloxane and/or (poly)organosiloxane nature:

R is a radical chosen from the group consisting of: halogens, iodine being more particularly selected, linear or branched alkyls containing 1 to 30 carbon atoms, $C_1$–$C_{30}$ aryls or $C_1$–$C_{30}$ aralkyls or alkylaryls; the halogens, the phenyls, the phthalates and the following radicals being adopted more specifically:

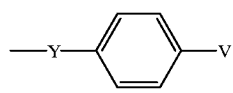

Y representing —$CH_2$—, —O— or —N=N— and V representing hydrogen, or Y representing —O—, —S— or —S—S— and V representing hydroxyl;

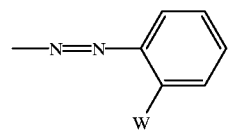

W representing hydrogen or carboxyl;

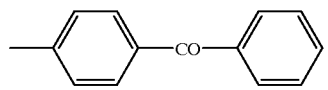

—CH=CH—Z, Z representing carboxyl or 2,4-dinitrophenyl; $CH_2CH_2COOC_2H_2$; or a $C_1$–$C_6$ alkyl;

A represents hydrogen, B represents a halogen or a $C_1$–$C_6$ alkyl and R represents a halogen;

A represents halogen; B represents hydrogen and R represents a halogen or a phenyl, or A represents hydrogen or a halogen and R and B together represent a chain which completes a naphthalene nucleus which, read in the direction from R to B, has the formula:

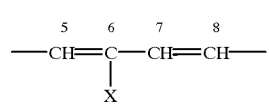

(2)

X representing hydrogen or a halogen, such that the compound of the formula (I) is a beta-naphthol of the formula:

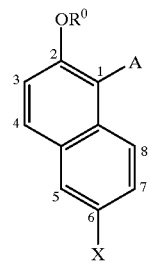

$R^0$, R, A and B being substituted or unsubstituted;

and in that it contains no hydrolytic enzyme which is capable of lysis of the bond between the oxygen and $R^0$ in —$OR^0$.

In its most general aspect, the present invention thus provides a perfected system of chemiluminescence or chemiluminometric analysis. It is based on the astonishing discovery of particular amplifiers which are derived from esters of halogenophenols (e.g. iodophenols) and which significantly improve the sensitivity of the luminescent reaction under consideration.

In the context of the present description, the term "improved" indicates that the total luminous emission of the luminescent reaction according to the invention and/or the signal/background noise ratio of the said reaction are superior to those achieved by the previously known systems.

Furthermore, in contrast to that advocated by some doctrines of the prior art, the chemiluminescent system according to the invention does not comprise hydrolytic enzymes intended to allow cleavage of the bond between the oxygen and the radical $R^0$ in the formula (I) to render the amplifier active. Moreover, the essence of the invention is radically opposed to that concept, since the aim is to obtain a minimum level of hydrolysis, which is synonymous with high performance of the amplification of the luminescence.

DETAILED DESCRIPTION OF THE INVENTION

Figure 1:
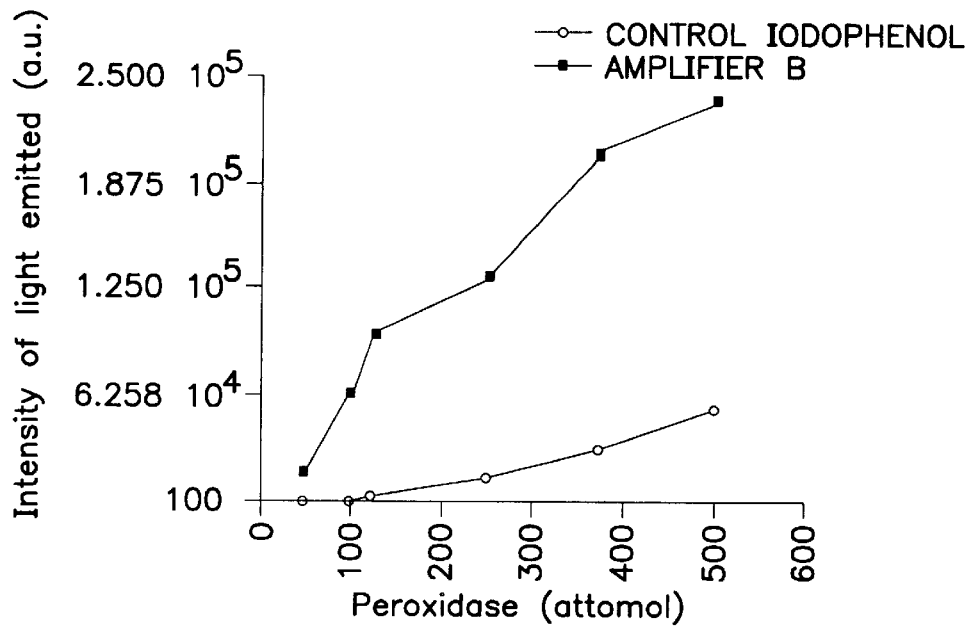

According to a preferred characteristic of the invention:

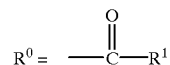

in formula (1) of the amplifier (e). In this case, the content of the non-hydrolysed ester:

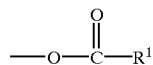

of the amplifier (e) is preferably greater than or equal to 40% by weight, preferably 60% by weight, and more preferably 90% by weight.

The present invention thus proceeds from advantageous and judicious selection of certain amplifier derived from phenols, and more especially consisting of esters of phenol (halogenophenols e.g.) with carboxylic acids, in particular mono-, di- or polycarboxylic acids, which are optionally functionalized, preferably by amine functional groups or also by aromatic radicals which carry one or more carboxylic acid functions.

The amplifier (e) used can be in the form of compounds of the formula (1) of the same nature or, advantageously, can comprise a mixture of at least one compound of the formula (1), preferably the esters in which:

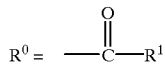

According to an interesting variant of the invention, in the case concerning a mixture of esters of the formula (1) as the amplifier (e), at least one of these esters preferably contains a substituent $R^1$ chosen from the radicals (i), (2i) and (3i), as defined above, and at least one other of these esters is distinguished by a substituent $R^1$ chosen from the radicals (4i) as defined above.

Regarding the ligand contained in the system according to the invention, this advantageously consists of at least one of the elements of the following pairs of substances which can be coupled:
antigen/antibody,
enzyme/substrate, enzyme/inhibitor,
receptor/ligand
lectin/sugar
nucleic acid/complementary nucleic acid.

These terms enzymes, substrates, antigens and antibodies can designate various products, such as proteins, hormones, haptens, steroids and metabolites, among others.

The luminescent chemical reagent (b) is a product which can lead to the excited state in the course of a chemiluminescence reaction, for example initiated by the product (OH') of an enzymatic reaction, and which then returns to the non-excited state after having emitted light or by emitting light. In the context of the invention, the chemiluminescent reagent (b) is preferably a product belonging to the family of 2,3-dihydro-1,4-phthalazinedione (DPD). More particularly, this DPD corresponds to the following general formula (2):

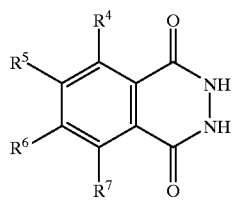

in which:
  $R^4$ represents a substituted or unsubstituted amine radical, and each of the radicals $R^5$, $R^6$ and $R^7$ represents H, a substituted or unsubstituted $C_1$–$C_6$ alkyl, a substituted or unsubstituted $C_1$–$C_6$ alkenyl, a hydroxyl, a $C_1$–$C_6$ alkoxy, a substituted or unsubstituted carboxyl or a substituted or unsubstituted amine radical,
  or $R^5$ represents a substituted or unsubstituted amine radical, and each of the radicals $R^4$, $R^6$ and $R^7$ represents H, a substituted or unsubstituted $C_1$–$C_6$ alkyl, a substituted or unsubstituted $C_1$–$C_6$ alkenyl, a hydroxyl, an alkoxy, a substituted or unsubstituted carboxyl or a substituted or unsubstituted amine radical,
  or $R^4$ and $R^5$ are taken together and represent an amino derivative which is unsubstituted or substituted by a benzo radical, and each of the radicals $R^6$ and $R^7$ represents H, substituted or unsubstituted $C_1$–$C_6$ alkyl, substituted or unsubstituted $C_1$–$C_6$ alkenyl, hydroxyl, alkoxy, substituted or unsubstituted carboxyl or a substituted or unsubstituted amine radical,
luminol and isoluminol being particularly preferred.

In the context of the present invention, the term "substituted amino" used in the legend of the formula (2) above also designates amido radicals.

In the case where a preferred reagent (b), that is to say luminol where $R^4$, $R^5$, $R^6$=H and $R^7$=NH$_2$, is present, this amino radical can serve as the coupling bridge of (b) with the ligand, directly or by the intermediary of a spacer compound of the type of those which are known and suitable, e.g. hemisuccinates, hemiglutarates, hemimaleates, carboxymethyl and glucuronyl derivatives and mercaptoacetates. After direct or indirect coupling of the ligand coupled to (b) with the species to be analysed, the analytical procedure will thus consist of reacting the chemiluminescent reagent (b), which has been fixed, with the other components of the system in a manner such that the coupling is indicated through the chemiluminescence reaction. The fixing of (b) on to the ligand represents only one of the method variants which can be envisaged.

In the context of the invention, the term enzyme designates both complete proteins and catalytic subunits.

The enzyme (c) preferably corresponds to an oxidoreduction enzyme as defined by the International Union of Biochemistry. This relates in particular to the enzymes of class 1, or oxidoreductases, of the International Union of Biochemistry classification.

An advantageous example of an oxidoreductase according to the invention is xanthine oxidase.

The enzyme (c) is more preferably selected from the peroxidases, such as horseradish peroxidase, microperoxidase, the peroxidase extracted from the microorganism *Arthromyces ramosus* and lactoperoxidase; horseradish peroxidase and microperoxidase being particularly preferred.

Like the chemiluminescent reagent (b), the enzyme (c) can optionally be coupled to the ligand, directly or indirectly, and thus constitutes a marker. Depending on the variants, this enzyme (c) may be in solution or also immobilized on a matrix.

In the preferred mode of carrying out the invention, the substrate (d) is an oxidant in the form of, preferably, a peracid or a peroxide, and more preferably hydrogen peroxide and/or an alkali metal perborate or alkaline earth metal perborate.

In fact, in the case where the chemiluminescent reagent is 2,3-dihydro-1,4-phthalazinedione (specifically luminol or isoluminol), this oxidant is converted, under the effect of the enzyme (c), into in an initiator (OH.) of oxidation of the reagent (b). As above, it can be envisaged that this oxidant is fixed directly or indirectly to the ligand, thus constituting a marker. According to one alternative, it can be part of the means of indication of the coupling by chemiluminescence which are used for reaction with the marker(s) carried by the ligand.

Regarding precisely the location of the components of the system according to the invention, the above shows that it is advantageous for at least one, and at most three, of these components (b) to (e) to be bonded (or carried by) the ligand (a), the other component or components being contained in the analysis medium.

Whatever the marker or markers of the ligand, it is preferable, according to the invention, that during the progress of the chemiluminescent analysis the system under consideration is combined with a solution comprising at least one pH regulator and/or at least one ionic strength regulator chosen from the salts, preferably the halides (advantageously chlorides), of alkali metals and/or alkaline earth metals, KCl, KBr, NaCl, CaCl$_2$ and CsCl being particularly preferred.

It has proved useful, in fact, for the pH of the analysis medium to be alkaline. Alkalinity is favourable to the luminescence reaction and also plays a role regarding the solubility of the amplifiers of the formula (1) and of the chemiluminescent reagent of the formula (2).

The pH regulation is therefore advantageously ensured by a regulator which consists of any suitable buffer, such as, for example, Tris buffer, carbonate buffer or phosphate buffer.

The ionic strength is also an important parameter of the analysis medium comprising the system according to the invention. In fact, it is determines the stability of the amplifiers (e) of the formula (1) with regard to hydrolysis of the radical OR$^0$, and more particularly the ester bond. It has been seen above that the lower the level of hydrolysis of the amplifiers (e) in the form of esters, the greater the luminescence performances.

The halides mentioned above thus advantageously ensure this function of regulation of the ionic strength. To this end, their amount is from 0.1 M to saturation, preferably 0.1 to 3 M.

There are of course secondary factors other than the pH and the ionic strength which are important for the chemiluminescent reaction to proceed well. There may be mentioned, among others, temperature, concentration of the components (b) to (e) of the system, the rate of mixing and the technique of measurement of the light.

These are the characteristics of the method and the analysis which fit in perfectly in the context of the present description, since it is noted that the present invention also relates to a method for qualitative and/or quantitative analysis of substances, preferably biological substances, by amplified chemiluminescence, characterized in that it comprises the system as defined above.

Generally, the conditions used in this method, and therefore the system described above, correspond to those used previously, in particular in the methods described in the patent EP 0 116 454 and in the application PCT WO 94/23 060. By reference, the corresponding parts of these documents are therefore integrated into the present description. To recap, it may be noted that the temperature of the analysis is advantageously between 10 and 50° C., and that the concentrations of components (b) to (e) of the system are the following:

reagent (b) (e.g DPD): 5 μmol–200 μmol/l, peroxidase (c): 0.1 ng to 5 g/l, oxidizing substrate (d): 10 μmol–30 mmol/l, amplifier (e): 1 μmol–100 mmol/l These concentrations are given with respect to the entire analysis medium, which advantageously comprises the aqueous buffered solution regulated a fortiori as defined above.

It is important to note that the exceptional efficiency of the amplifiers (e) according to the invention enables reductions in the concentration of enzyme to be envisaged. It is in fact possible to manage with concentrations of between 0.1 ng and 1 μg/l. This represents not insignificance savings in consumables.

The reaction according to the preferred embodiment of the invention can be outlined as follows:

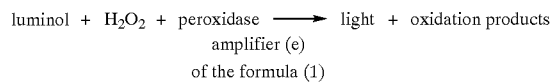

Industrial Application

Under another of its advantageous aspects, the present invention also provides a kit for qualitative and/or quantitative analysis of substances, preferably biological substances, by amplified chemiluminescence, characterized in that it comprises the system as defined above.

The system, the method and the kit according to the invention have immediate and obvious applications in the field of biochemical and biological analysis. In fact, they can readily be incorporated in the context of techniques of immunological, immunoenzymatic, immunohistological, enzymatic and genetic analyses.

It is important to note that the indication systems can include recognition systems of the ligand/receptor, sugar/lectin, enzyme/substrate and enzyme/inhibitor type, for example: membrane receptors, hormones, neurotransmitters and, generally, signal transducers.

These can be, for example, "ELISA" techniques of the competitive or non-competitive type, of the sandwich type, of the "western, northern & southern blot" type or of the immunohistological type (antibody/marked antigen or nucleic probe).

The substances to be analysed can thus be contained;

on or in solid supports chosen, preferably, from the following list:
  whole or divisible microtitration plates,
  test tube of a synthetic polymer or glass,
  biological polymers,
  immunohistology sections,
  membranes,
  beads etc.
or in liquid supports of the solution, emulsion or dispersion type forming part of the analysis medium.

The solid supports are used in so-called heterogeneous, heterogeneous competitive or also heterogeneous two-site analytical procedures. The liquid media are more suitable for so-called homogeneous phase analytical procedures.

The system and the method according to the invention can also be used to identify and analyse in a biological medium, substances such as peroxidases or endogenous peroxides (H$_2$O$_2$). These are substances which correspond to one or more of the constituents of the analysis system.

The examples which follow will allow better understanding of the invention and reveals all its use advantages and variants.

EXAMPLES

I—Description of the Figures

FIG. 1 attached shows the curves of the intensity of the emitted light (IEL) in arbitrary units (a.u.) as a function of the amount of peroxidase enzyme used in attomol for iodophenol (curve-□-control) and for the iodophenyl butyrate amplifier B of example 1 (curve-■-amplifier B).

Figure 2:
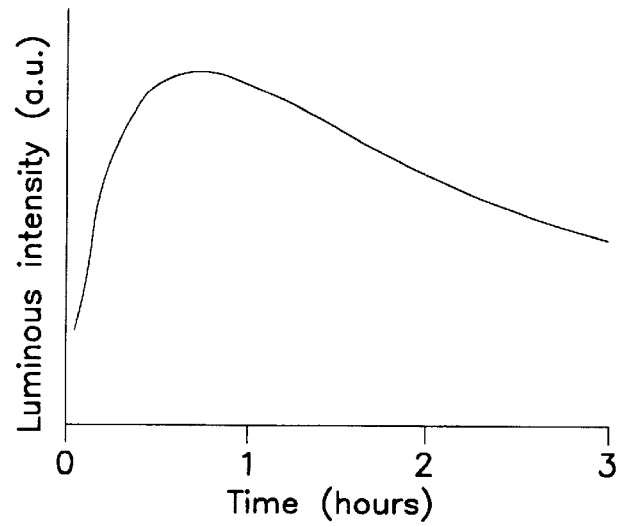

FIG. 2 attached represents the kinetics of the emission of light in the presence of amplifier (B) by means of a graph of the luminous intensity emitted, expressed in arbitrary units (a.u.), as a function of the time in hours under the conditions of example 16.

Figure 3:
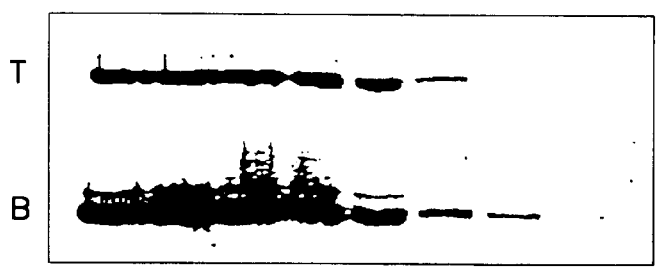

FIG. 3 attached shows the western blot results obtained with iodophenyl butyrate [amplifier (B)] compared with the results obtained with the control iodophenol.

Figure 4:
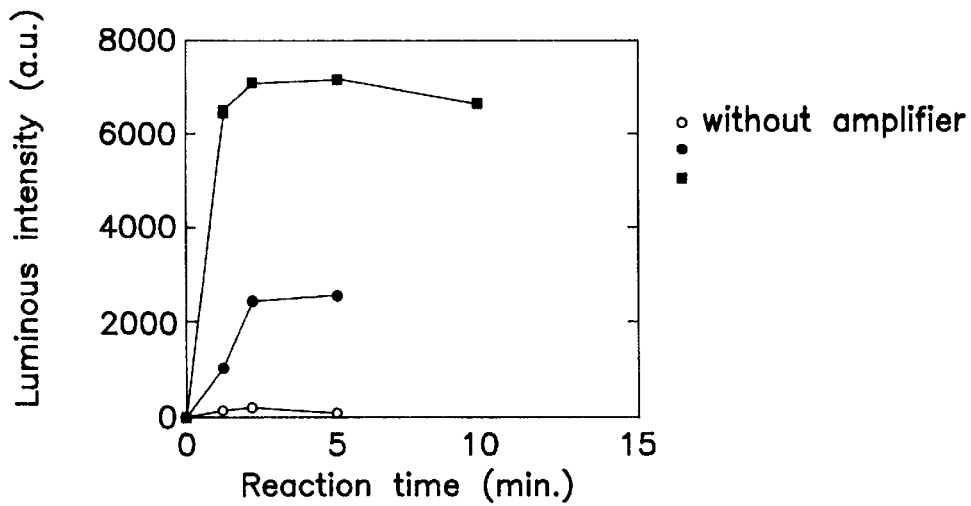

FIG. 4 attached represents the kinetics of the emission of light in the presence of amplifier B of example 1 [-■-(B)] in comparison with a positive control: iodophenol amplifier [-●-control ⊕], and with a negative control without amplifier [-O-control O], by means of graphs of the luminous intensity in arbitrary units (a.u.)=f(t) (t in min) under the conditions of example 18.

Figure 5:
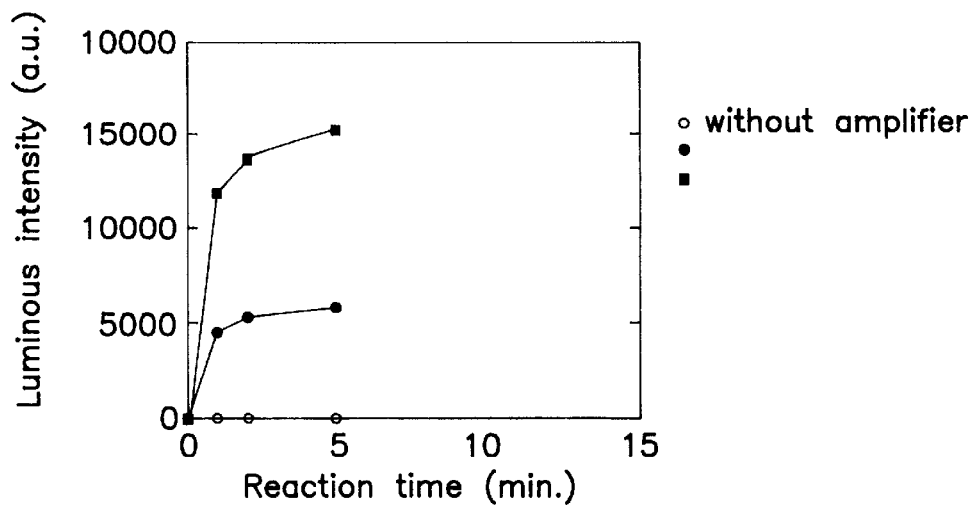

FIG. 5 attached represents the kinetics of the emission of light in the presence of amplifier B of example 1 [-■-(B)] in comparison with a positive control: amplifier iodophenol [-●-control ⊕] and with a negative control without amplifier [-O-control O] by means of graphs of the luminous intensity in arbitrary units (a.u.)=f(t) (t in min) under the conditions of example 19.

Figure 6:
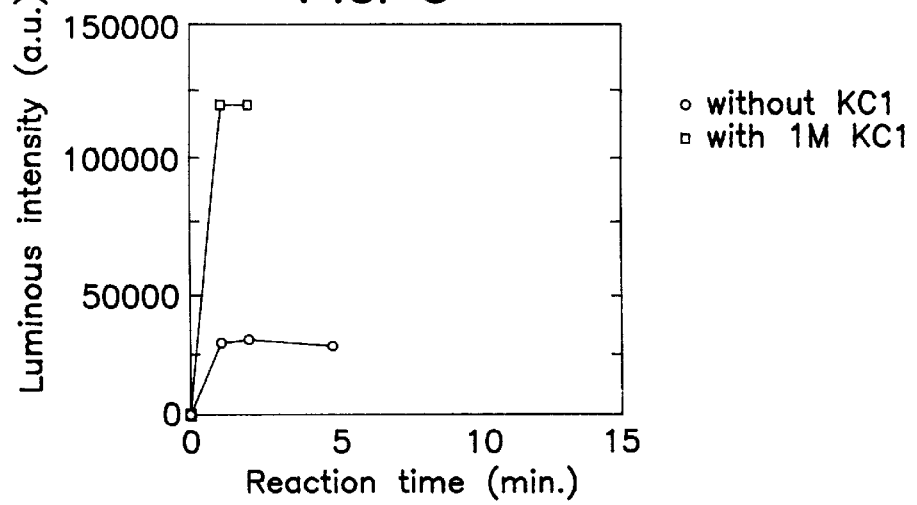

FIG. 6 attached represents the kinetics of the emission of light in the presence of amplifier A of example 1 with an ionic strength: KCl 1 M graph [-☐-] and without an ionic strength [graph-O-] by means of graphs of the luminous intensity in arbitrary units (a.u.)=f(t) (t in min) under the conditions of example 20.

II—Materials and Methods

Reagents

All the following products originate from Sigma Chimie, France: horseradish peroxidase (HRP) type VI, luminol (5-amino-2,3-dihydro-1,4-phthalazinedione), tris (hydroxymethyl)aminomethane, hydrogen peroxide 30%, potassium chloride and dimethylsulphoxide (DMSO).

All the products used for the chemical syntheses originate from Aldrich, France.

The rabbit anti-c-met polyclonal antibody originates from Santa Cruz Biotechnology, USA; the goat anti-rabbit polyclonal antibody marked with peroxidase originates from CovalAb, LYON, FRANCE. Nitrocellulose membrane (Schleicher and Schuell, ECQUEVILLY, FRANCE), Kodak film X-OMAT AR X-Ray (ROCHESTER, N.Y., USA).

Equipment for the Analysis

The chemiluminescence reactions were carried out in 4 ml polystyrene tubes and in 4 ml glass (borosilicate glass) tubes (Costar Sc. Co., USA). The light emitted was measured using two luminometers; TLXI monotube (L9990120-2121) (Dynatech Laboratories, France) and Biolumat LB9500 Berthold, France. Materials for the polyacrylamide gel electrophoresis and the transfer originate from Biorad Laboratories, France.

The infra-red (IR) spectra were plotted on a Perkin Elmer spectrometer model 1310 and expressed in $cm^{-1}$.

The nuclear magnetic resonance spectra ($^1$H-NMR) were plotted on a Bruker AC200 spectrometer, and the chemical shifts are indicated in ppm with respect to tetramethylsilane as the internal reference.

The separations by liquid chromatography are carried out on a silica column of Merck Kieselgel 60 (70–230 mesh ASTM).

III—Synthesis and Hydrolysis of Amplifiers (e) According to the Invention (esters of 4-iodophenol)

Example I

Synthesis of 4-Iodophenyl Acetate (Amplifier A) and 4-Iodophenyl Butyrate (Amplifier B)

6.5 mmol (1.5 eq) of chloride of the corresponding acid are added dropwise to a solution of 1 g 4-iodophenol (4.5 mmol) in 10 ml pyridine kept at 0° C. After 3 hours at room temperature, the solution is poured into 100 ml of a 0.5 M hydrochloric acid solution. After extraction with ethyl ether (2×50 ml), the organic phase is washed with water, then with a sodium bicarbonate solution and finally with water. After drying over magnesium sulphate, the solvent is evaporated off and the residue is purified by chromatography over silica, eluent ethyl ether/pentane 5–95. Yield: 75 to 90%.

4-IODOPHENYL ACETATE: m.p.=27° C.

IR (film): 1755 $cm^{-1}$

NMR $CDCl_3$): 2.28, s, 3 H; 6.86, m, 2H; 7.68, m, 2H.

4-IODOPHENYL BUTYRATE: m.p.=34° C.

IR (film): 1755 $cm^{-1}$.

NMR ($CDCl_3$): 1.03, t, 3 H, 1.76, sex, 2 H; 2.52, t, 2H,; 6.85, m, 2H; 7.67, m, 2H.

Example 2

Synthesis of Succinic Acid Mono(4-Iodophenyl) Ester (Amplifier C)

0.10 g sodium (4.5 mmol) is added to a solution of 1 g 4-iodophenol (4.5 mmol) in 25 ml anhydrous ether under a nitrogen atmosphere, while stirring. When the sodium has disappeared, 0.5 g (4.5 mmol) succinic anhydride dissolved in benzene is added. The mixture is stirred at room temperature for 24 hours. The gelatinous sodium salt is filtered off, washed with anhydrous ether and then dissolved in water. After acidification with 0.5 M hydrochloric acid, the acid ester is extracted with ether and the solution is dried. After acidification with 0.5 M hydrochloric acid, the acid ester is extracted with ether and the solution is dried. After evaporation of the solvent, the residue is recrystallized in a mixture of hexane/benzene.

Weight obtained: 0.4 g.

m.p.=145° C.

IR ($CCl_4$): 1745, 1705$^{-1}$

NMR ($CDCl_3$): 2.6 to 2.9, m, 4H; 7.0, m, 2H; 7.68, m, 2H.

Example 3

Synthesis of Adipic Acid Mono(4-Iodophenyl) Ester (Amplifier D)

Adipic acid (0.66 g, 4.5 mmol), 4-iodophenol (1 g, 4.5 mmol) and one drop of 98% sulphuric acid are added to 20 ml toluene. The solution is heated under reflux and the water formed is removed by a Dean-Stark apparatus (24 hours). The majority of the toluene is evaporated off and the remaining solution is then poured in to 50 ml of a vigorously stirred saturated solution of sodium bicarbonate. The aqueous solution is extracted twice with ether and then acidified to pH 4 with 1 M hydrochloric acid. The acid solution is extracted with chloroform (2×50 ml) and the chloroform phases are combined and dried. After evaporation of the solvent, the residue is recrystallized from a mixture of benzene/hexane. Weight obtained: 0.37 g.

m.p.=89° C.

IR ($CCl_4$): 1745–1705 $cm^{-1}$

NMR ($CDl_3$): 1.6 to 1.8, m, 4H; 2.43, t, 2H; 2.58, t, 2H; 7.06, m, 2H; 7.67, m, 2H.

Example 4

Hydrolysis of the 4-Iodophenyl Esters (A) and (B) in a Buffer Solution of pH=8.6

4.1 Operating Method

A test solution S1 is first prepared, comprising:

TRIS buffer: 0.1 M-pH: 8.6;

luminol: 1.2 mM.

A solution S2 also comprising potassium chloride in a concentration of 3 M is also prepared.

Operating Method

These solutions $S_1$ and $S_2$ are mixed with amplifiers (e) A and B from example 1 concentrations (conc.) and are stored at 4° C. for several days before analysis.

The proportions of iodophenol and ester are then determined by gas phase chromatography (GPC). This phenol/ester analysis is carried out as indicated below:

10 ml of solution, 1 ml of a solution of thymol in methanol of concentration 1 mg/ml and 50 ml ethyl ether are stirred; 50 g sodium sulphate are added. The ethereal phase is drawn off and the solid is rinsed with 50 ml ether; the ethereal phases are combined and then concentrated to about 2 ml. 0.5 µl is injected in the GPC.

4.2 Results

The results of the analysis are given in table 1 below

TABLE 1

| TEST | SAMPLES | CONC (mg/10 ml) | % iodophenol | % ester |
|---|---|---|---|---|
| 1 | $S_1$ with A | 9 | 85 | 15 |
| 2 | $S_2$ with A | 17 | 50 | 50 |
| 3 | $S_1$ with A | 1.2 | 75 | 25 |
| 4 | $S_2$ with A | 0.9 | 55 | 45 |
| 5 | $S_1$ with B | 19.5 | 3.7 | 96.3 |
| 6 | $S_2$ with B | 20 | 2.5 | 97.5 |
| 7 | $S_1$ with B | 0.95 | 10 | 90 |
| 8 | $S_2$ with B | 1.25 | 4 | 96 |

It can be seen that in a basic medium, the halide or halides of $S_2$ and the alkaline slow down the rate of hydrolysis of the esters.

III—Chemiluminescence

Examples 5 to 9

Chemiluminescence Reaction Amplified by Esters of Iodophenol 0.112 mmol luminol and 0.068 mmol control iodophenol (example 5) and various amplifiers (e) (A, B, C, D of examples 1 to 3)=examples 6 to 9 are added to 100 ml Tris buffer 0.1 M pH 8.6. The solution is prepared several hours before its use and stored at 4° C. 10 µl $H_2O_2$ at 20 mM are added to 0.9 ml of this solution. A first measurement of the emission of light is carried out and corresponds to the background noise. 50 µl peroxidase at $10^{-9}$ g/ml are added to this same tube and the emission of light was then measured. The results of these tests are shown in table 2 below.

TABLE 2

Amplification of the luminous intensity by esters of iodophenol.

| EXAMPLE | AMPLIFIER | BACKGROUND NOISE (a.u.) | SIGNAL (a.u.) | SIGNAL/ BACKGROUND NOISE RATIO |
|---|---|---|---|---|
| 5 | control (4-iodophenol) | 1475 | $0.028.10^7$ | 193 |
| 6 | A | 8432 | $0.45.10^7$ | 533 |
| 7 | B | 2432 | $0.45.10^7$ | 1597 |
| 8 | C | 2699 | $0.89.10^7$ | 3306 |
| 9 | D | 4661 | $1.43.10^7$ | 3086 |

Legend: a.u. = arbitrary units

Examples 10 to 14

Effect of the Ionic Strength on the Amplification of the Chemiluminescence Reaction The procedures of examples 5 to 9 are repeated in the presence of 2M potassium chloride. The results of these tests are shown in table 3 below.

TABLE 3

Effect of the increase in the ionic strength on the amplification of the chemiluminescent reaction

| EXAMPLE | AMPLIFIER | BACKGROUND NOISE (a.u.) | SIGNAL (LUR) (a.u.) | SIGNAL/ BACKGROUND NOISE RATIO |
|---|---|---|---|---|
| 10 | control (4-iodophenol) | 23327 | $0.52.10^7$ | 222 |
| 11 | A | 17402 | $1.92.10^7$ | 1104 |
| 12 | B | 12882 | $3.83.10^7$ | 2973 |
| 13 | C | 6197 | $3.65.10^7$ | 5891 |
| 14 | D | 6770 | $1.69.10^7$ | 2510 |

Example 15

Comparative Study of the Amplified Chemiluminescence Reaction Using Peroxidase at Various Concentrations The procedures of examples 5 to 8 are repeated, but only with iodophenol and isdophenol butyrate B. The concentration of the peroxidase was reduced, using 50 to 500 ($10^{-12}$ mol). The results of these tests are shown in FIG. 1 attached.

It is found that amplifier (B) of the invention is undeniably more effective than the control iodophenol.

Example 16

Kinetic Study of the Amplified Chemiluminescence Reaction

The procedures of examples 5 to 9 are repeated using only iodophenyl butyrate (amplifier B of example 1). The emission of light was measured every 20 seconds for 3 hours. The results of these tests are shown FIG. 2 attached.

Example 17

Comparative Study of the Amplified Chemiluminescence on the Detection of Cell Protein by the Western Blot Method The oncogen c-met codes for a heterodimeric protein of 190 kD in human thyroid papillary carcinomas (B-CPAP) (C. Paulin et al., Int. J. Oncology, 7; 657–660 (1995)). These cells were used to detect the c-met protein in accordance with the protocol described by C. Paulo et al. The following total amounts of cell proteins were used: 50 µg; 40 µg; 30 µg; 20 µg; 10 µg; 5 µg; 2.5 µg and 1 µg.

The technique of polyacrylamide gel electrophoresis described by Laemmli, Nature 227, 680 (1970) was used to separate the cell proteins and transfer them to the nitrocellulose membrane. The membrane is then treated with various reagents under the following conditions: Saturation of non-specific sites on the membrane with 5% skimmed milk in PBS buffer for 30 min. Incubation of the membrane with rabbit anti-c-met antibodies for 1 hour at 37° C. Washing in PBS/Tween 0.2% and incubation with goat anti-rabbit polyclonal antibody marked with peroxidase for 1 hour at 37° C. After four washings of 5 min in PBS/Tween 0.3%, the membrane is immersed in the chemiluminescent reagent described in examples 5 to 9 for 3 min. The membrane is then drained and subsequently covered with a plastic film and exposed to an X-ray film for a duration ranging from 30 seconds to one hour, and then developed. More precisely, FIG. 3 attached represents the indication by western blotting of the c-met protein (145 kDa) in the cell lysate with the amplifier B and with a control amplifier iodophenol. The chemiluminescent reagent used is identical to that used in examples 5 to 9.

On this FIG. 3, the numbers noted on the top longitudinal edge correspond to the total amounts of protein (TAP) contained in the cell lysate deposited in each track. The TAP are given in micrograms (μg).

The line T corresponds to the control iodophenol and the line B to the amplifier (e) according to the invention as synthesized in example 1 and designated by the letter B.

A start of indication for a TAP of 1 μg and a clear indication for TAP=2.5 μg, as regards the test carried out with the amplifier (B), is found.

For the control T, however, the first detection appears only at a TAP of 5.

This clearly shows the extreme sensitivity of the system according to the invention.

Examples 18 to 20

Comparative Study of the Amplified Chemiluminescence Using Peroxidase Bonded to an Anti-mouse Antibody for Detection of Murine Immunoglobulins 1-Experimental Protocol 100 μl of a solution of murine immunoglobulins at 1 mg/ml (carbonate buffer 50 mM pH 8.5) are introduced into a polystyrene measuring tube. This solution is then incubated for 2 h at 37° C.

After incubation, the tube is emptied of its solution and then washed with 500 μl TRIS-HCl buffer 50 mM pH 8.5.

100 μl anti-mice antibodies marked with peroxidase, of the type of those marketed by COVALAB, are introduced into this washed tube on which the murine immunoglobulins have been fixed. These 100 μl Ab are diluted to 1/50,000 in TRIS-HCl buffer. This tube is then incubated for 1 h at 37° C. Two washings are carried out as indicated above. Finally, 500 μl chemiluminescent reagent containing amplifiers A or B of example 1 above are then introduced into the tube containing the complexes of Ag (murine Ig)/Ab marked with peroxidase.

The composition of this chemiluminescent reagent is identical to that of the reagent used in examples 5 to 9 above.

The tube is agitated and the result is read with the aid of a Biolumat LB 9500 luminometer from Berthold France.

Three different tests are carried out for examples 18 to 20:
Example 18: Amplifier B without an ionic strength
Example 19: Amplifier B with an ionic strength (KCl 3M)
Example 20: Amplifier A with and without an ionic strength (KCl 1M).

2-Results

FIGS. 4, 5 and 6 attached give an account of the results obtained.

FIGS. 4 and 5 clearly show that the amplifier B causes an increase in the emission of light which is at least 3 times greater than that induced by the control

What is claimed is:

1. A composition for qualitative and/or quantitative analysis of biological substances by amplified chemiluminescence comprising a) at least one ligand capable of coupling to the biological substance, b) at least one cyclic diacylated dihydrazide fused to an aromatic chemiluminescence reagent, c) an oxido reduction luminescence enzyme, d) at least one oxidizing agent specific to enzyme c) and e) at least one amplifier of luminescence of the formula

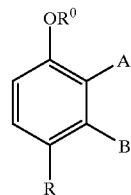

wherein $R^0$ is selected from the group consisting of

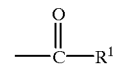

and polyorganosiloxane, $R^1$ is selected from the group consisting of alkyl of 1 to 10 carbon atoms, alkylcarboxyl of 2 to 10 carbon atoms, alkylamino and aminoalkyl of 1 to 10 carbon atoms, aryl, alkylaryl and aralkyl, R is selected from the group consisting of halogen, alkyl of 1 to 30 carbon atoms, aryl of 6 to 30 carbon atoms, aralkyl of 7 to 30 carbon atoms, alkylaryl of 7 to 30 carbon atoms,

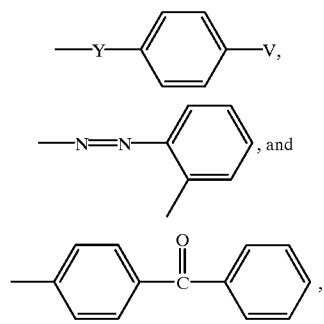

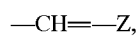—CH=—Z,

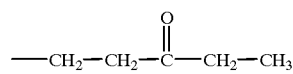

and alkyl of 1 to 6 carbon atoms, wherein W is hydrogen or carboxyl and Z is carboxyl or 2,4-dinitrophenyl, Y is selected from the group consisting of —CH$_2$—, —O— and —N=N— and V is hydrogen or Y is selected from the group consisting of —O—, —S— and —S—S and V is —OH, one of A and B is hydrogen and the other is halogen or A is hydrogen or halogen and R and B together form

and X is hydrogen or halogen.

2. A composition of claim 1 wherein R is

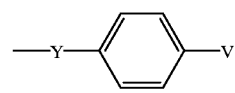

Y is selected from the group consisting of —CH$_2$—, —O— and —N=N— and V is hydrogen or Y is selected from the group consisting of —O—, —S— and —S—S— and V is —OH.

3. A composition of claim 1 wherein R is selected from the group consisting of

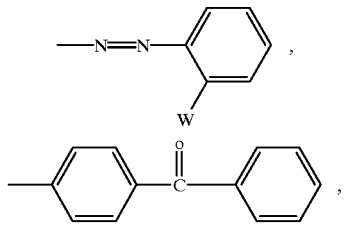

—CH=CH—Z, —CH$_2$—CH$_2$—C—OCH$_2$—CH$_3$ and alkyl of 1 to 6 carbon atoms, W is hydrogen or carboxyl and Z is carboxyl or 2,4-dinitrophenyl.

4. A composition of claim 1 wherein the e) amplifier is at least 40% by weight of the composition.

5. A composition of claim 1 wherein the e) amplifier is at least 90% by weight of the composition.

6. A composition of claim 1 wherein e) is a mixture of at least two esters where R$^0$ is

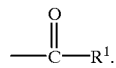

7. A composition of claim 6 wherein one R$^1$ is selected from the group consisting of alkyl of 1 to 10 carbon atoms, alkylcarboxy of 2 to 10 carbon atoms and aminoalkyl and alkylamino of 1 to 10 carbon atoms and the second R$^1$ is selected from the group consisting of phenyl, aryl, alkylaryl and aralkyl.

8. A composition of claim 1 wherein component b) has the formula

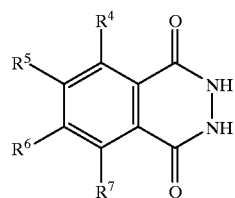

wherein R$^4$ is NH$_2$ and R$^5$, R$^6$ and R$^7$ are individually selected from the group consisting of hydrogen, alkyl of 1 to 6 carbon atoms, alkenyl of 2 to 6 carbon atoms, —OH, alkoxy of 1 to 6 carbon atoms, carboxyl and —NH$_2$ or R$^5$ is —NH$_2$ and R$^4$, R$^6$ and R$^7$ are individually selected from the group consisting of hydrogen, alkyl of 1 to 6 carbon atoms, alkenyl of 2 to 6 carbon atoms, —OH, alkoxy of 1 to 6 carbon, atoms, —COOH and —NH$_2$ or R$^4$ or R$^5$ are amino unsubstituted or substituted by phenyl and R$^6$ and R$^7$ are individually selected from the group consisting of hydrogen, alkyl of 1 to 6 carbon atoms, alkenyl of 2 to 6 carbon atoms, —OH, alkoxy of 1 to 6 carbon atoms, —COOH and —NH$_2$.

9. A composition of claim 1 wherein the chemiluminescence enzyme c) is selected from the group consisting of oxidoreductase and xanthine oxidase.

10. A composition of claim 9 wherein enzyme c) is selected from the group consisting of horseradish peroxidase, micro peroxidse, lacto peroxidase and peroxidase extracted from *Arthromyces ramosus*.

11. A composition of claim 1 wherein the oxidizing agent d) is selected from the group consisting of hydrogen peroxide, an alkali metal perborate and an alkaline earth metal perborate.

12. A composition of claim 1 in an aqueous solution containing an alkali metal halide or alkaline earth metal halide.

13. A composition of claim 12 wherein the halide is present in an amount of 0.1 M to saturation.

14. A composition of claim 1 wherein ligand a) comprises at least one of the elements of a pair of substances selected from the group consisting of antigen/antibody, enzyme/substrate, enzyme/inhibitor, receptor/ligand, lectin/sugar and nucleic acid/complementary nucleic acid which can be coupled.

15. An analysis kit comprising a composition of claim 1 and the substances to be analyzed are contained:

on or in solid supports selected from the group consisting of
whole or divisible microtitration plates,
test tubes of synthetic polymer or glass
biological polymers,
immunohistology sections,
membranes and
or in liquid media of the solution, emulsion or dispersion type, forming part of the analysis medium.

* * * * *